(12) United States Patent
Bretschneider et al.

(10) Patent No.: US 8,935,155 B2
(45) Date of Patent: Jan. 13, 2015

(54) METHOD FOR PROCESSING MEDICAL REPORTS

(75) Inventors: Claudia Bretschneider, Schlieben (DE); Sonja Zillner, München (DE)

(73) Assignee: Siemens Aktiengesellschaft, Munich (DE)

( * ) Notice: Subject to any disclaimer, the term of this patent is extended or adjusted under 35 U.S.C. 154(b) by 217 days.

(21) Appl. No.: 13/619,337

(22) Filed: Sep. 14, 2012

(65) Prior Publication Data

US 2014/0081623 A1    Mar. 20, 2014

(51) Int. Cl.
*G06F 17/27* (2006.01)
(52) U.S. Cl.
USPC .................................. 704/9; 704/1; 704/270
(58) Field of Classification Search
CPC ....... G06F 17/271; G06F 17/27; G06F 17/21; G06F 17/2785; G06F 17/277; G06F 17/2755
USPC ......................................... 704/9, 1, 270–275
See application file for complete search history.

(56) References Cited

U.S. PATENT DOCUMENTS

| | | | | |
|---|---|---|---|---|
| 6,055,494 | A * | 4/2000 | Friedman | 704/9 |
| 6,556,964 | B2 * | 4/2003 | Haug et al. | 704/9 |
| 7,080,004 | B2 * | 7/2006 | Wang et al. | 704/9 |
| 7,191,119 | B2 * | 3/2007 | Epstein et al. | 704/10 |
| 7,657,521 | B2 * | 2/2010 | Masarie et al. | 707/771 |
| 2004/0243545 | A1 * | 12/2004 | Boone et al. | 707/2 |
| 2005/0154580 | A1 * | 7/2005 | Horowitz et al. | 704/9 |
| 2006/0253273 | A1 * | 11/2006 | Feldman et al. | 704/9 |
| 2008/0010059 | A1 * | 1/2008 | Mohri | 704/9 |
| 2008/0312954 | A1 * | 12/2008 | Ullrich et al. | 705/2 |

OTHER PUBLICATIONS

Bretschneider, C., Zillner, S., Siemens, A. G., & Hammon, M. Grammar-Based Lexicon Extension for Aligning German Radiology Text and Images.*
Fan, J. W., & Friedman, C. (2011). Deriving a probabilistic syntacto-semantic grammar for biomedicine based on domain-specific terminologies. Journal of biomedical informatics, 44(5), 805-814.*

(Continued)

*Primary Examiner* — Douglas Godbold
(74) *Attorney, Agent, or Firm* — King & Spalding L.L.P.

(57) ABSTRACT

A method for processing medical reports includes applying natural language processing methods to perform an initial segmentation of at least parts of textual contents of each medical report into information units, thereby identifying information units, such as text fragments, sentences or text passages, within the medical reports. The information units are classified into at least one context class to determine their appropriate context classes for a particular situation or application. The context classifications are created using a grammar, e.g., a context-free grammar, and can then be used for automatically assigning each information unit to an appropriate context meta-information. The medical report may be annotated by assigning the information units to context meta-information determined by the context class, and the context meta-information may be used by other applications, e.g., dedicated mechanisms for clinical data integration, how to efficiently handle the available information units within medical reports.

11 Claims, 1 Drawing Sheet

(56) References Cited

OTHER PUBLICATIONS

Kate, R. J. (Dec. 2011). Unsupervised grammar induction of clinical report sublanguage. In ICMLA (2) (pp. 53-58).*

Xu, H., AbdelRahman, S., Lu, Y., Denny, J. C., & Doan, S. (2011). Applying semantic-based probabilistic context-free grammar to medical language processing—A preliminary study on parsing medication sentences. Journal of biomedical informatics, 44(6), 1068-1075.*

* cited by examiner

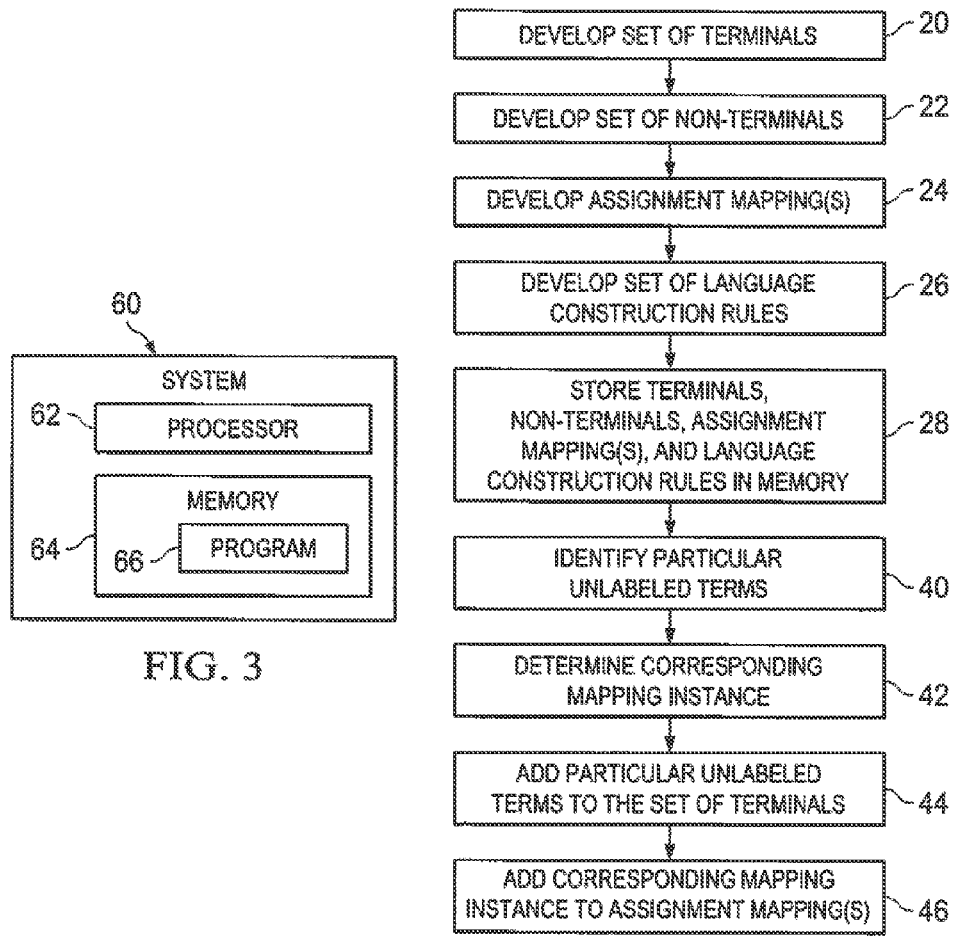

METHOD FOR PROCESSING MEDICAL REPORTS

TECHNICAL FIELD

The present disclosure relates to a method for processing medical reports. More particularly, the present disclosure relates to a method of processing textual contents of medical reports on the basis of a grammar. The disclosure further relates to a development of such a grammar.

BACKGROUND

Medical reports including clinical information and patient reports are currently provided in heterogeneous formats and structures.

Accordingly, there is a need in the art to gain access to such medical reports for the purpose of using their textual contents by machine-operated systems. Addressing the overall aim of providing means for the seamless integration of patient data it is particularly important to identify information units within these reports which are of high relevance for later diagnosis decisions.

However, clinicians are usually required to provide a comprehensive medical report of any finding in order to verify the completeness of a diagnosis. Besides pathological findings, which are of particular interest for later diagnosis decisions, medical reports usually also include non-pathological findings. Thus, the requirement of comprehensiveness eventually results in extensive texts in which relevant information units are usually difficult to identify.

SUMMARY

In one embodiment, a method for processing medical reports comprises: a) segmenting at least parts of textual contents of the medical report into information units by applying natural language processing methods; b) classifying the information units into at least one context class using a context-free grammar, the grammar specifying language construction rules within a specific medical domain; and c) annotating the medical report by assigning at least one of said information units to at least one context meta-information determined by said context class.

In another embodiment, a method for developing a grammar for specifying language construction rules of information units comprises: a) developing a set of terminals, each terminal comprising at least one term defined by a medical domain terminology; b) developing a set of non-terminals, comprising b1) a first subgroup, the first subgroup comprising context classes of the medical domain; and b2) a second subgroup, the second subgroup comprising at least one interims constituent; c) developing at least one assignment mapping for the mapping of each term of said terminals onto at least one non-terminal of said set of non-terminals; d) developing a set of said language construction rules, comprising d1) at least one construction rule specifying an association of at least one of said information units to at least one of said context classes; and/or d2) at least one construction rule specifying an association of at least one of said context classes to an ordered list of elements of the set of said non-terminals and/or d3) at least one construction rule specifying an association of at least one of said interims constituents to an ordered list of elements of the set of said non-terminals.

In a further embodiment, the method comprises enhancing said set of construction rules with probabilistic information by determining a frequency of occurrence of particular construction rules. In a further embodiment, the method comprises enhancing said assignment mapping with probabilistic information by determining a frequency of occurrences of mappings between individual concepts of said set of terminals to said context classes or sub-classes thereof. In a further embodiment, the method comprises:
extending said set of terminals and said assignment mappings; identifying unlabeled terms being no element of the set of terminals and being an element within at least one information unit; determining the corresponding mapping instance by using the frequency information of occurrences of construction rules; adding the unlabeled terms to the set of terminals; and adding a corresponding mapping instance to said at least one assignment mapping. In a further embodiment, the method comprises integrating expert knowledge into the grammar in order to extend the set of terminals and/or the construction rules and/or the assignment mappings of the grammar. In a further embodiment, the method comprises processing an automatic classification of at least one medical report by applying an extended set of terminals using a parsing algorithm.

In another embodiment, a method for processing medical reports as disclosed above is performed concurrently with a method for developing a grammar as disclosed above.

In another embodiment, a grammar for specifying language construction rules of information units comprises: a) a set of terminals, each terminal comprising at least one term defined by a medical domain terminology; b) a set of non-terminals, comprising b1) a first subgroup, the first subgroup comprising context classes of the medical domain; and; b2) a second subgroup, the second subgroup comprising at least one interims constituent; c) at least one assignment mapping for the mapping of each term of said terminals onto at least one non-terminal of said set of non-terminals; d) a set of said language construction rules, comprising d1) at least one construction rule specifying an association of at least one of said information units to at least one of said context classes; and/or d2) at least one construction rule specifying an association of at least one of said context classes to an ordered list of elements of the set of said non-terminals and/or d3) at least one construction rule specifying an association of at least one of said interims constituents to an ordered list of elements of the set of said non-terminals.

In another embodiment, a computer program product contains a program code stored on a computer-readable medium and which, when executed on a computer, carries out any of the methods disclosed above. In another embodiment, a data storage carrier stores such a computer program to cause a computer to perform any of the methods disclosed above.

BRIEF DESCRIPTION OF THE DRAWINGS

Embodiments of the present disclosure may be better understood with reference to the accompanying drawings, in which:

FIG. 1 shows an example method for processing medical reports, according to one embodiment, FIG. 2 shows an example method for processing medical reports, according to another embodiment, and FIG. 3 shows an example system for performing any of the steps of the example methods of FIGS. 1 and 2.

DETAILED DESCRIPTION

Some embodiments provide for processing medical reports in order to handle their textual contents by machine-operated systems. Embodiments can take advantage of an existing grammar for processing the medical reports, or, for concurrently developing a grammar by an accompanying learning and developing procedure.

In one embodiment, a method for processing medical reports is disclosed. By applying natural language processing methods, an initial segmentation of at least parts of textual contents of the medical report into information units is carried out, thereby addressing the challenge of identifying information units, such as text fragments, sentences or text passages, covered within medical reports that are of relevance for a particular context.

In a second step, the information units are classified into at least one context class in order to determine their appropriate context classes for a particular situation or application. The context classifications are created using a grammar, e.g., a context-free grammar. Said context classifications can then be used for automatically assigning each information unit to an appropriate context meta-information.

Specifically, in a third step, the medical report is annotated by assigning at least one of said information units to at least one context meta-information determined by said context class. The context meta-information may be used by other applications, such as dedicated mechanisms for clinical data integration, in order to efficiently handle the available information units within medical reports.

According to an embodiment, a grammar for specifying language construction rules of information units comprises a set of terminals, each terminal comprising at least one term defined by a medical domain terminology. The grammar further comprises a set of non-terminals whereby a first subgroup comprises context classes of the medical domain and a second subgroup comprises at least one interims constituent. The interims constituent may be supporting a definition of said construction rules of the grammar. The grammar further comprises an assignment mapping for the mapping of each term of said terminals onto at least one non-terminal and a set of said language construction rules whereby at least one construction rule specifying an association of an information unit to at least one context classes and whereby, additionally or alternatively, at least one construction rule specifying an association of a context class to an ordered list of freely definable elements of non-terminals.

The foregoing is a summary and thus contains, by necessity, simplifications, generalizations, and omissions of detail; consequently, those skilled in the art will appreciate that the summary is illustrative only and is not intended to be in any way limiting. Other aspects, inventive features, and advantages of embodiments of the present invention are become apparent in view of the non-limiting detailed description set forth below.

Processing Medical Reports

According to an embodiment, a method for processing medical reports is proposed. This embodiment relies on natural language processing methods, or NLP, establishing means for extracting and structuring text-based information. NLP methods generally reflect particularities of an underlying domain, which is, in the context of the embodiment, a clinical domain represented by medical reports. Thus, the proposed method relies on NLP methods that can be used or customized for extracting and structuring information from clinical texts in order to make the extracted medical data available for usage in other clinical applications or processes.

The proposed method further relies on a context free grammar, or CFG, for applying and, according to an alternative embodiment, developing the grammar.

A medical report is generally understood herein as any text written or dictated by clinicians in the clinical setting for describing patients, their pathologies or their personal, social, and medical histories or findings, said text written or dictated during interviews or during procedures.

The general concept of the proposed method is to identify information units, such as text passages, sentences or text fragments, within medical reports and to automatically classify the information units according to their relevance in a particular context. As clinicians, nurses, etc. are required to document the condition and status of patients in a very comprehensive and detailed manner, it is very likely that such reports encompass large amounts of information whereby a majority of this information is of no relevance for subsequent diagnose and treatment decision. For instance, normal findings are usually documented for completeness but do not cover any relevant information for later decisions.

On the basis of the proposed method, it is possible to distinguish between at least two context classes of context-relevance, for instance pathological sentences and non-pathological sentences within a radiology report. The context classes may be distinct to each other.

Meta-information about the context class can then be used for subsequent processing steps according to further embodiments, such as the context-dependent seamless integration of information with other clinical applications or external knowledge resources.

For instance, a text string in a radiology report which is identified as an anatomical concept—i.e. a concept of a base lexicon describing a particular anatomy of the human body—within a pathological sentence—i.e. a sentence that has been classified to the context class >>pathologic<<—would be enhanced by a link enabling a human to easily access a corresponding position in an associated medical image.

According to another example, the context meta-information is used to automatically select the kind or type of information source a particular concept within the medical report should be linked to. In this example, each identified text string in the medical report that is identified as anatomical concepts in sentences of the context class >>pathologic<< would be linked to an information source which covers related background information about pathologies of the respective anatomical entity.

If the identified text string would occur in a sentence of a context class >>non-pathologic<<, the text string would be linked to a different information source that covers detailed information about statistics illustrating the involvement of the particular anatomical entity in a wide range of diseases.

In the following, the proposed method is described referring to the FIG by a process comprising computational and interactive steps.

In a first step 1, textual contents of the medical report are segmented in information units, e.g., meaningful information units. One way of accomplishing this segmentation step 1 is to focus on the regular sentence structure by using the full stop as indicator. However, depending on the sentence construction style of clinical text documents, other indicators for separating meaningful information units might be even more appropriate. For recognizing the boundaries of the meaningful information units a combination of NLP technologies, such as pattern recognition and exclusion is used. Special patterns such as dates, measurements and abbreviations are part of the sentence but do not necessarily contain segmentation indicators and are therefore excluded.

In a second step 2, identified information units are classified into at least one context class. Within this step, any of the identified information units, i.e. segmented text strings, sentences, etc., are classified according to the context classes. For each application, the appropriate context classes will be defined. For establishing the context class during the classification process, a dedicated grammar is used.

In a third step 3, the medical report is annotated by assigning the information units to at least one context meta-information determined by the context class. Within this step, an annotation mapping, or, in other words an annotation with context-relevance meta-information, is established.

Establishing a Grammar

In the following, an embodiment is described by which a grammar, specifically a context-free grammar, is established. The grammar is used by the method for processing medical reports.

An underlying assumption for establishing the context categories is that a clinician's expressions differ according to the particular high-level semantic of information which are to be conveyed by the clinician.

For instance, pathological and non-pathological findings differ clearly in their way they are described. Non-pathological findings are usually formulated very briefly. Further, non-pathological findings usually encompass negations. By contrast, pathological findings are likely to contain more than 12 words and contain positive, i.e. not negated, pathological findings which may follow the pre-defined medical terminology rules.

In other words, the high-level semantic of the content to be conveyed—i.e. the context category such as pathological or non-pathological findings—influences the way how clinicians built up sentences or sentence fragments. Thus, analyzing the way how sentences are constructed allows a determination of the context category of information units within a report.

The first step for classifying information units is to define a finite set of context classes along with their semantic meaning as well as their relevance for the current application context. The set of context classes is defined as subgroup of the set of non-terminals N of the grammar.

A dedicated context-free grammar is used to implement the semantic specification of context categories. The grammar of a domain specifies the rationale of how information units—such as sentences or sentence fragments—are built up. In other words, the grammar specifies the construction rules of information units.

For each grammar the following building blocks are required:
a) a set of terminals $T=\{w_1, w_2, w_3, \ldots\}$ with $w_i$ being terms of the domain. The set of terminals T may be also referred to as >>basis lexicon<< or >>domain terminology<<. An initial set of terminals T can be fine-tuned in a subsequent learning and developing procedure as shown below.
b) a set of non-terminals N encompassing a first subgroup of context classes $CON_1, CON_2, \ldots, CON_N$ as well as a second group of other interims constituents required for defining the grammar construction rules.
c) an assignment mapping m: $T \rightarrow N$ that maps each term $w_i \in T$ being an element of the set of terminals onto at least one non-terminal of set N. The assignment mapping m may be also referred to as >>classification of domain terminology<<. An initial assignment mapping m can be fine-tuned in a subsequent learning and developing procedure as shown below.
d) a set of construction rules R that specify how basic information units S are constructed by using various context class as well as interims constituents:
Examples of construction rules R in the set of construction rules R are given below.

A first exemplary rule $S \rightarrow CON_1$ specifies an association of an information unit S to a context classes $CON_1$. A second exemplary rule
$S \rightarrow CON_2$ associates an information unit S to a context classes $CON_2$. This association may be likewise continued until a n-th rule $S \rightarrow CON_n$.

A further exemplary rule $CON_i \rightarrow n_1 n_2 n_3 \ldots n_j$ specifies an association of at least one context class $CON_i$ to an ordered list of elements $n_1 n_2 n_3 \ldots n_j$ of the set of non-terminals N.

In other words, formulated in pseudo-code:
Forall i with $n_1, \ldots n_j$ an ordered list of elements of N specifying the construction rule of any information unit of the context class $CON_i$.

A further exemplary rule $n_k \rightarrow m_1 m_2 m_3 \ldots m_l$ specifies an association of at least one non-terminal $n_k$ of the set of non-terminals N to an ordered list of interims constituents $m_1 m_2 m_3 \ldots m_k$ of the set of interims constituents.

In other words, formulated in pseudo-code:
forall k with $m_1 m_2 m_3 \ldots m_k$ an ordered list of elements of N specifying the construction rule of any information unit of the interims construct $n_k$.

A grammar distinguishing between >>pathological<< and >>non-pathological<< information units a medical report can be exemplarily defined as follows:
$T=\{w_1, w_2, w_3, \ldots\}$ with $w_i$ terms that belong to the domain terminology, e.g. using a specific medical taxonomy.
N={MODIFIER, TERM_PATH, DISEASE, ANATOMY, PATHOLOGIC, NON-PATHOLOGIC, MOD_NOPATH, NEGATION, ...}
Rules:
S→PATHOLOGIC
S→NONPATHOLOGIC
NONPATHOLOGIC→NEGATION PATHOLOGIC
NONPATHOLOGIC→MOD_NOPATH ANATOMY
PATHOLOGIC→DISEASE
PATHOLOGIC→TERM_PATH
DISEASE→MODIFIER DISEASE In order to establish the grammar, an establishment of a basis lexicon, i.e. the set of terminals, is required. For addressing the particularities of a domain, herein a specific medical domain, an approach for generating a context-free grammar is constraint to a well-defined sublanguage, i.e. a technical language that is used by the various actors in the medical domain to pass specific messages.

In each sublanguage, different words might be used and those words can have particular meanings. A basis lexicon that encompasses the majority of words including their meaning of the domain is established. For building up such a basis lexicon, existing medical ontologies, dictionaries and/or domain models formally capturing the domain knowledge can be used either individually or several ontologies can be used in combination. The domain knowledge generally includes hierarchical structuring of concepts along with relationships between concepts.

In a further step in establishing the grammar the assignment mapping is established. Said assignment mapping can rely on an initial user input with a minimum extent. Specifically, highest-level concepts of a hierarchical medical ontology may be classified by an initial categorization of a user by mapping a context class or a sub-class of a context class to a set of non-terminals N of the grammar.

Within the example used above, a highest level concept of a taxonomy would be mapped as being either of context class >>pathologic<< or of class >>non-pathologic<<.

Any children of high-level concepts are computed automatically by means of an algorithm shown in pseudo code below:

Forall c, d with c being direct or indirect child concepts of d and d being highest-level concept and K being the assigned context class or subclass of d, then c is of class K as well.

In other words the underlying algorithm specifies that the classification of the highest-level concept is inherited by all the children concepts.

Learning and Developing Procedure

According to an alternative embodiment, a learning and developing procedure is provided. The learning and developing procedure aims to enhance the usability of the grammar.

According to a further embodiment, manually annotated texts for training an existing grammar are used in order to augment an existing grammar into a probabilistic context-free grammar, which is captioned by probabilistic CFG or PCFG. The probabilistic context-free grammar is augmented with probabilistic parameters by counting a frequency of usage of each construction rule.

Within the learning and developing procedure several embodiments may be accomplished individually or in combination:

- the basis lexicon, i.e. the set of terminals of the grammar, is extended;
- the assignment mapping, i.e. the classification of domain terminology, is extended and instances of the assignment mapping are amended and/or corrected; and;
- the construction rules are additionally labeled with the information about their occurrence frequency.

An application of the learning and developing procedure is exemplarily described by a following scenario. Medical reports are manually annotated—i.e. manually annotated with classification information—by domain experts using the established context classes. A parsing algorithm uses an existing assignment mapping to derive the context classes of each word and, further on, uses the probabilities of a probabilistic context free grammar, or PCFG, to calculate the most likely way to form a grammar-conform sentence out of the given information unit.

The parsing algorithm further includes all possible derived parse trees for the defined information unit representing possible ways to construct the unit and also indicating the context class or context classes.

If there was more than one parse tree derived, and therefore also more than one information class derived with the given grammar, the class with the highest computed probability is assumed to be the one matching for the information unit and the unit will be classified accordingly.

This learning and developing procedure grants a fine-tuning of context categories. For implementing the learning and developing procedure, information about the occurrence frequencies of parse trees is used. For calculating the occurrence frequency, manual annotated clinical text documents are used as input. The learning and developing procedure leads to an improvement of an established grammar and thus of the established classification approach, whereby the improvement is attained on three levels:

- On a sentence level by enhancing the set of construction rules by probabilistic information. On the basis of manually annotated medical reports, the learning and developing procedure is able to count the frequency of occurrence of particular construction rules. The information about statistical frequency is used as decision criteria for the disambiguation of ambiguous classification results within a training process.
- On the word level by enhancing the assignment mapping. On the basis of the manually annotated clinical text documents, the learning and developing procedure is able to count the frequency of occurrences of mappings between individual concepts of the basis lexicon to context classes or subclasses. The information about the statistical frequency is used as decision criteria for the disambiguation of ambiguous assignment mappings.
- On the word level by extending the basis lexicon. Unlabeled words—i.e. words being no element of the set of terminals T AND words contained within at least one classified information unit—are first identified and added to the set of terminals. In a following step, the information about the frequency of construction rules is used to determine their corresponding assignment mapping and respectively, the corresponding mapping instance is added to the assignment mapping.

According to a further embodiment, expert knowledge can be integrated into an established grammar in order to extend and/or fine-tune the basis lexicon, i.e. the set of terminals T, the construction rules R and the assignment mappings m of the established grammar.

According to a further embodiment, an automatic classification of medical reports is carried out. The set of medical reports is automatically classified by applying the extended basis lexicon, the assignment mappings and the specified construction rules using a parsing algorithm. The input is a set of medical reports. The output is a set of classified medical reports. In the classified medical reports an assigned context class for each information unit is formally captured.

According to a further embodiment, the context class is used for improved information access. Accordingly, the meta-information determined by the context class assigned to information units is used for subsequent processing steps, such as the context-dependent seamless information access to other clinical applications or external knowledge resources.

FIG. 2 shows an example method for processing medical reports, according to one embodiment. The method includes developing an initial grammar (indicated at 10) and developing the initial grammar, e.g., by a learning and developing process (indicated at 12). Developing the initial grammar may begin at step 20, in which a set of terminals is developed, each comprising at least one term defined by a medical domain terminology. At step 22, a set of non-terminals is developed, comprising (a) a first subgroup comprising context classes of the medical domain and (b) a second subgroup comprising at least one interims constituent. At step 24, at least one assignment mapping is developed for the mapping of each term of said terminals onto at least one non-terminal of said set of non-terminals. At step 26, a set of language construction rules is developed, which include at least one of (a) at least one construction rule specifying an association of at least one of said information units to at least one of said context classes, (b) at least one construction rule specifying an association of at least one of said context classes to an ordered list of elements of the set of said non-terminals, and (c) at least one construction rule specifying an association of at least one of said interims constituents to an ordered list of elements of the set of said non-terminals. At step 28, the set of terminals, the set of non-terminals, the at least one assignment mapping, and the set of said language construction rules are stored in memory.

Developing the initial grammar may include a learning and developing process, e.g., as disclosed herein. For example, at step 40, unlabeled terms being no element of the set of terminals and being an element within at least one information unit may be identified. At step 42, the corresponding mapping instance may be determined by using the frequency information of occurrences of construction rules. At step 44, the unlabeled terms may be added to the set of terminals, and at step 46, a corresponding mapping instance may be added to the at least one assignment mapping.

Any of the steps of the method of FIG. 2 may be performed by executing a program/software including instructions for performing the respective step(s).

FIG. 3 shows an example computer system 60 for performing any of the steps of the example methods of FIGS. 1 and 2 discussed above. Computer system 60 may include a processor 62 and a memory device 64 storing a program or software application 66 that is executable by processor 62 to perform any of the methods steps shown in FIG. 1 and/or FIG. 2.

In summary, some embodiments provide a method of development of a grammar that allows distinguishing information units along their context relevance. The development of a grammar can be used to e.g. distinguish between pathological and non-pathological sentences in medical reports.

As there are various styles in medical reports, a grammar suiting all kinds of medical reports is practically impossible. A developed grammar rather needs to reflect the style of processed medical reports, the information needs of a user as well as the particularities of the domain terminologies. For this reason, one embodiment provides an approach for developing a grammar allowing to automatically distinguishing information units between application relevant context categories.

Further embodiments extend the approach for developing a grammar by providing a dedicated learning and developing procedure. The learning and developing procedure may be of particular advantage in extending an underlying domain language. Currently, there is a lack of language-specific dictionaries in the medical domain. In this field of endeavor, some embodiments provide approaches extending the currently available domain terminologies.

Some embodiments can be implemented in computing hardware (computing apparatus) and/or software, including but not limited to any computer or microcomputer that can store, retrieve, process and/or output data and/or communicate with other computers.

The processes can also be distributed via, for example, downloading over a network such as the Internet. A program/software implementing the embodiments may be recorded on computer-readable media comprising computer-readable recording media. The program/software implementing the embodiments may also be transmitted over a transmission communication media such as a carrier wave.

Certain embodiments are described in detail above, but it will be understood that variations and modifications can be effected within the spirit and scope of the invention covered by the claims.

What is claimed is:

1. A computer-implemented method for processing medical reports, comprising:
   using a processor, executing computer-readable instructions stored in non-transitory commuter-readable media to perform the steps of:
   a) segmenting at least parts of textual contents of a medical report into information units by applying natural language processing methods;
   b) classifying particular information units into either a pathological context class or a non-pathological context class using a context-free grammar specifying language construction rules within a specific medical domain, wherein the language construction rules are configured to classify each particular information unit as either a pathological finding or a non-pathological finding based on at least one of:
      a structure of a sentence defined by the particular information unit;
      a structure of a sentence fragment defined by the particular information unit;
      a number of words defined by the particular information unit; and
      the presence of negations in the particular information unit; and
   c) annotating the medical report by assigning at least one of said information units to at least one context meta-information determined by said context class.

2. A computer-facilitated method for developing a grammar for specifying language construction rules of information units, the method comprising:
   using a processor, executing computer readable instructions stored in non-transitory computer readable media to perform the steps of:
   1) developing an initial grammar by:
      a) developing a set of terminals, each terminal comprising at least one term defined by a medical domain terminology;
      b) developing a set of non-terminals, comprising:
         b1) a first subgroup, the first subgroup comprising context classes of the medical domain; and
         b2) a second subgroup, the second subgroup comprising at least one interims constituent;
      c) developing at least one assignment mapping for the mapping of each term of said terminals onto at least one non-terminal of said set of non-terminals;
      d) developing a set of said language construction rules, comprising at least one of:
         d1) at least one construction rule specifying an association of at least one of said information units to at least one of said context classes; and
         d2) at least one construction rule specifying an association of at least one of said context classes to an ordered list of elements of the set of said non-terminals; and
         d3) at least one construction rule specifying an association of at least one of said interims constituents to an ordered list of elements of the set of said non-terminals; and
      e) storing the set of terminals, the set of non-terminals, the at least one assignment mapping, and the set of said language construction rules in memory, and
   2) automatically developing the initial grammar by executing computer-readable instructions stored in non-transitory computer-readable media, using a processor, to extend said set of terminals and said assignment mappings by:
      a) identifying unlabeled terms being no element of the set of terminals and being an element within at least one information unit;
      b) determining the corresponding mapping instance by using the frequency information of occurrences of construction rules;
      c) adding the unlabeled terms to the set of terminals; and
      d) adding a corresponding mapping instance to said at least one assignment mapping.

3. The method of claim 2, comprising enhancing said set of construction rules with probabilistic information by determining a frequency of occurrence of particular construction rules.

4. The method of claim 2, comprising enhancing said assignment mapping with probabilistic information by determining a frequency of occurrences of mappings between individual concepts of said set of terminals to said context classes or sub-classes thereof.

5. The method of claim 2, comprising integrating expert knowledge into the grammar in order to extend the set of terminals and/or the construction rules and/or the assignment mappings of the grammar.

6. The method of claim 2, comprising processing an automatic classification of at least one medical report by applying an extended set of terminals using a parsing algorithm.

7. A computer program product stored on a non-transitory computer-readable medium and which, when executed on a computer, carries out a method comprising:
   a) developing a set of terminals, each terminal comprising at least one term defined by a medical domain terminology;
   b) developing a set of non-terminals, comprising:
      b1) a first subgroup, the first subgroup comprising context classes of the medical domain; and
      b2) a second subgroup, the second subgroup comprising at least one interims constituent;
   c) developing at least one assignment mapping for the mapping of each term of said terminals onto at least one non-terminal of said set of non-terminals;
   d) developing a set of said language construction rules, comprising at least one of:
      d1) at least one construction rule specifying an association of at least one of said information units to at least one of said context classes; and
      d2) at least one construction rule specifying an association of at least one of said context classes to an ordered list of elements of the set of said non-terminals; and
      d3) at least one construction rule specifying an association of at least one of said interims constituents to an ordered list of elements of the set of said non-terminals; and
   e) extending said set of terminals and said assignment mappings by a process including:
      e1) identifying unlabeled terms being no element of the set of terminals and being an element within at least one information unit;
      e2) determining the corresponding mapping instance by using the frequency information of occurrences of construction rules;
      e3) adding the unlabeled terms to the set of terminals; and
      e4) adding a corresponding mapping instance to said at least one assignment mapping.

8. The computer program product of claim 7, further operable to enhance said set of construction rules with probabilistic information by determining a frequency of occurrence of particular construction rules.

9. The computer program product of claim 7, further operable to enhance said assignment mapping with probabilistic information by determining a frequency of occurrences of mappings between individual concepts of said set of terminals to said context classes or sub-classes thereof.

10. The computer program product of claim 7, further operable to integrate expert knowledge into the grammar in order to extend the set of terminals and/or the construction rules and/or the assignment mappings of the grammar.

11. The computer program product of claim 7, further operable to process an automatic classification of at least one medical report by applying an extended set of terminals using a parsing algorithm.

* * * * *